United States Patent [19]
Sullivan

[11] Patent Number: 5,183,095
[45] Date of Patent: Feb. 2, 1993

[54] MEANS FOR PRODUCING HIGH PRECISION CASTINGS

[76] Inventor: Michael R. Sullivan, 1620 East La Donna La., Tempe, Ariz. 85283

[21] Appl. No.: 621,280

[22] Filed: Nov. 30, 1990

[51] Int. Cl.⁵ .................. B29C 33/52; B29C 39/26
[52] U.S. Cl. .................. 164/34; 164/DIG. 4; 249/54; 249/61; 249/72; 249/134
[58] Field of Search ............ 164/DIG. 4, 34; 249/61.54, 134, 34, 72, 62

[56] References Cited

U.S. PATENT DOCUMENTS

| | | | |
|---|---|---|---|
| 1,639,416 | 8/1927 | Spiro | 164/DIG. 4 |
| 2,765,831 | 10/1956 | Tupper | 220/306 |
| 3,182,358 | 5/1965 | Van Rossem | 249/54 |
| 3,531,013 | 9/1970 | Hammes | 220/306 |
| 3,610,317 | 10/1971 | Benfield | 249/54 |
| 3,939,898 | 2/1976 | Petro et al. | 164/DIG. 4 |
| 4,081,019 | 3/1978 | Kulig | 164/244 |
| 4,161,208 | 7/1979 | Cooper | 164/DIG. 4 |
| 4,210,258 | 7/1980 | Von Holdt | 220/306 |
| 4,558,841 | 12/1985 | Engelmann et al. | 164/DIG. 4 |
| 4,573,921 | 3/1986 | Berger | 164/244 |
| 4,777,996 | 10/1988 | Finelt | 249/54 |
| 4,962,909 | 10/1990 | Kohler | 164/DIG. 4 |

*Primary Examiner*—Willard Hoag
*Attorney, Agent, or Firm*—Richard R. Mybeck

[57] ABSTRACT

The production of high precision molds and castings for dental prosthesis and the like is enhanced with a casting ring and sprue former base constructed of a clear expandable thermoplastic. The ring and base are telescopically interlockable with each other to define a vessel containing a mold form strategically disposed therein so that as investment solution poured throughout is able to cure without detracting from the precise measurements of the mold form to provide a true mold from which precisely dimensioned castings are formed.

10 Claims, 1 Drawing Sheet

WAX OUT

MEANS FOR PRODUCING HIGH PRECISION CASTINGS

INTRODUCTION

The present invention relates generally to the art of precision molding and more particularly to a combination sprue former and casting ring made from a transparent elastic thermoplastic and capable in use to form castings requiring precise and close dimensional tolerances, such as are required for dental inlays and the like.

BACKGROUND OF THE INVENTION

Various means and methods have heretofore been proposed for preparing castings, and molds therefore, using the so-called "lost wax" method. Use of the lost wax method within the dental profession for the purpose of casting crowns and other such dental restorations is similarly well known. Of particular note with regard to dental castings is the fact that dental castings require extreme accuracy for the final product to be both useful and comfortable. Heretofore, metallurgical characteristics have virtually dictated that the castings be prepared from precious metals such as gold. Numerous attempts have been made at preparing dental castings from base metal alloys but experience has shown that base metal castings generally require excessive finish work to allow the restoration to fit properly.

Another problem inherent in these casting techniques utilizing the lost wax method is the fact that curing of the investment material is an exothermic reaction and as the investment material hardens, heat is generated. This heat then causes "swelling" of the investment material which, when using conventional rigid casting rings and sprue formers, results in at least some compression on and distortion of the wax model within the investment. Any degree of compression against the wax model while preparing a dental restoration is unacceptable because it will distort the restoration pattern and ultimately impair the fit of a casting produced therefrom. Thus, when the pattern is burned out and molten metal is introduced into the void formed within the hardened investment material, the casting thereby created will not correspond exactly to the original pattern. This results not only in discomfort to the patient for whom the restoration has been prepared, but unnecessary expenditure of time, energy and money for the patient, the dentist, and the dental technician to modify the dimensions of the casting so that it will fit reasonably properly.

The problem of obtaining accurately dimensioned castings is further magnified when utilizing base metal alloys wherein the only effective solution heretofore available required detailed and expensive hand finishing of the castings or the taking of completely new impressions and making new castings until a satisfactory result is obtained. An unacceptable alternative required the patient to accept an inferior final product. It is toward the resolution of these prior art problems in producing accurately dimensioned castings in an economically viable manner that the present invention is directed.

BRIEF SUMMARY OF THE INVENTION

The present invention comprises means and methods for preparing dental castings and like precisely dimensioned objects by the lost wax method which can be precisely and predictably dimensioned including a sprue former and casting ring which are constructed from a transparent elastic thermoplastic such as polyvinylchloride (PVC), Polymethylmethacrylate (PMMA), polyacrylonitrile, polypropylene and like materials.

The use of a transparent elastic thermoplastic, for which polyvinylchloride ("PVC") will be recited as typical, to create the sprue former and casting ring has provided two significant advantages over the prior art methods. First, a transparent sprue former and casting ring to form a cup allows for a more accurate use of investment solution. Obviously the creation of the mold will fail if insufficient investment solution is used while the use of excess investment solution is wasteful and requires unnecessary curing time.

Second, particularly in the dental field, extreme dimensional accuracy is required. The setting and curing of the investment solution is an exothermic reaction. If the mold cup cannot uniformly absorb the stresses and forces generated thereby, such forces and stresses will be directed inwardly to the paraffin form thereby causing deformities in the mold being created. It has been discovered that the elastic thermoplastics when used herein in the manner described, will uniformly expand in response to the action of the investment solution during curing so that all of the forces of expansion are absorbed by the sprue cup and not by the mold.

Accordingly, a primary object of the present invention is to provide new and improved means and methods for producing lost wax castings which insures the accuracy and hence the dimensional integrity of the mold produced thereby and hence the casting produced therefrom.

Another object of the present invention is to provide a combination sprue former and casting ring for lost wax casting procedures which enables precise amounts of investment solution to be added thereto and which, during curing is able to uniformly absorb the expansion of the curing investment without altering the dimensional integrity of the mold produced thereby.

Still a further object of the present invention is to provide means and methods for producing precisely dimensioned casting by lost wax procedure which castings are equally suitable for dental reconstructions and fine jewelry.

These and still further objects as shall hereinafter appear are readily fulfilled by the present invention in a remarkably unexpected manner as will be readily discerned from the following detailed description of an exemplary embodiment thereof especially when read in conjunction with the accompanying drawing in which like parts bear like numerals throughout the several views.

DESCRIPTION OF THE PREFERRED EMBODIMENT

Figure 1:
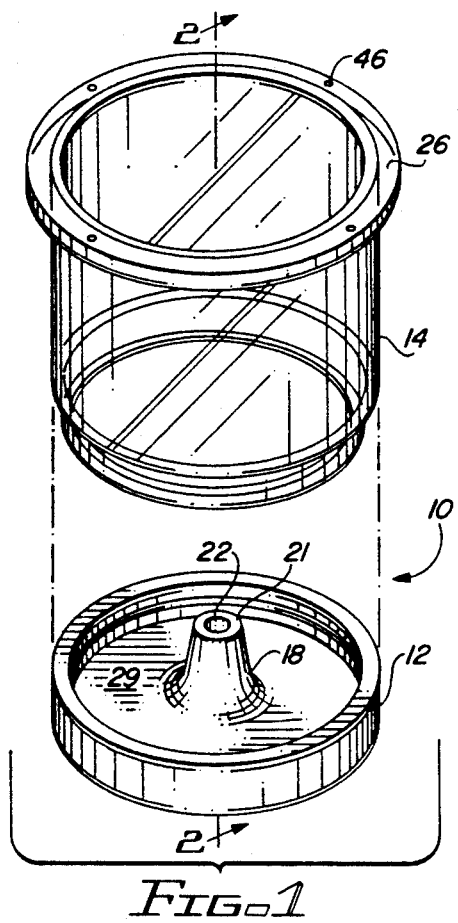
FIG. 1 is an isometric view of a device embodying the present invention for producing high precision castings.
Figure 2:
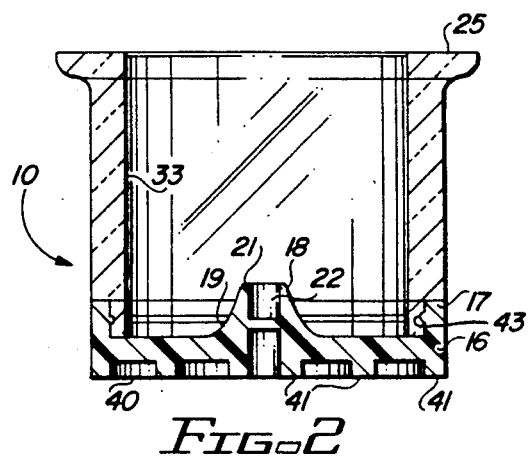
FIG. 2 is a cross-sectional view of the device of FIG. 1 taken on line 2—2 thereof.

An assembly embodying the present invention is identified in the accompanying drawing by the general reference 10. Each assembly 10 comprises a sprue former base 12 and a casting ring 14. The sprue former base 12 comprises a generally circular body portion 16 having an annular upstanding flange 17 disposed in circumscription thereabout and a generally conical member 18 disposed in the center therefore. Conical member 18 has a base portion 19 and an inwardly and upwardly tapering exterior surface 20 terminating in a top 21 into which a downwardly extending cylindrical cavity 22 is disposed for a purpose to be hereinafter described in greater detail.

Casting ring 14 comprises an inwardly and downwardly tapering body portion 24 having an outreaching annular flange 25 integrally formed with the upper edge 26 thereof and extending generally normal therefrom and a depending flange member 27 extending axially from body portion 24 and adapted to be seated within base 12 in dual surface-to-surface sealing engagement therewith, the lower edge 28 of body portion 24 engaging the upper surface 29 of flange 17 and the leading edge 30 of flange 27 engaging the upper surface 31 of body portion 16.

Sprue base 12 and casting ring 14 are each constructed from a transparent elastic thermoplastic such as polyvinylchloride (PVC) polymethylmethacrylate (PMMA), polyacrylonitrile, polypropylene and like material having a glass transition temperature of between about 25° C. and about 105° C. and a melting point greater than the exothermic temperature of the chosen investment material. Of course each of the aforementioned plastics will contain a suitable plasticizer such as dibutyl phthalate, dioctylphthalate, nylon 610 or the like. In use, casting ring 14 is disposed upon and nested within sprue base 12 to form assembly 10 as will now be described.

When ring 14 is placed upon sprue base 12, the lower edge 28 of casting ring 14 engages the upper surface 31 of body portion 16 in intimate investment-tight contact. The volume defined by device 10 between surface 31 and fill line 32 within body portion 16 is filled with a solution of a suitable investment 34.

Investment 34 may be any of the conventional compositions commonly used for lost wax casting. One such suitable composition is known by the brand name CB-30 and is manufactured by CMP Industries, Inc., Albany N.Y. CB-30 is a phosphate bound cristobalite. Another suitable investment is marketed under the brand name Accufit ® by PreVest Inc. of Cleveland, Ohio.

In the preparation of assembly 10, sprue forming base 12, and casting ring 14 are provided with a unique interlock which is created by forming an annular head 43 upon the inner surface of flange 17 which coacts with a complementary and corresponding groove 44 formed on the outer surface 45 of depending flange 27 so that when casting ring 14 is telescopically inserted into ring 14 until edge 30 engages surface 31, head 43 will snap into groove 44 forming a liquid tight seal therewith.

Figure 3A:
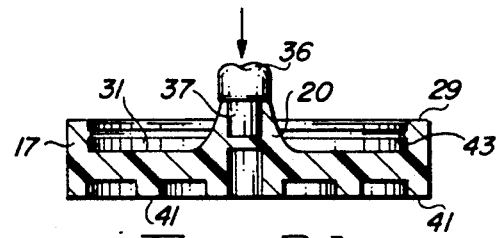
FIG. 3A is a cross-sectional view of a sprue former with a positive form in place according to the present invention.
Figure 3B:
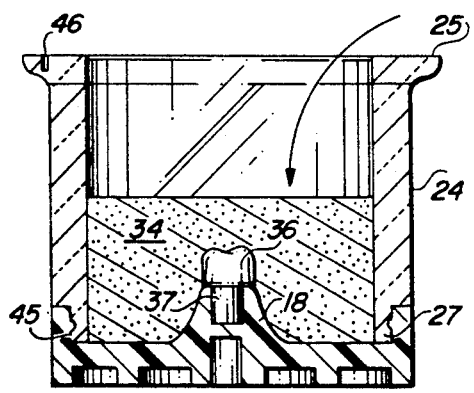
FIG. 3B is a cross-sectional view of casting ring sealingly-fitted into the sprue former of FIG. 3A and partially filled with investment solution.

In one practice of the present invention, a positive form 36 made out of paraffin or other similar material is shaped, as by carving, to conform to the desired casting. Form 36 will have a shank or sprue 37 depending therefrom. Form 36 is then securely mounted into base 19 by inserting sprue 37 into cavity 22. Ring 14 is then securely attached to base 12 in circumscription about form 36 to define assembly 10. A solution of investment 34 is then prepared as needed and poured into the vessel defined by and in assembly 10 up to fill line 32 as shown in FIG. 3B and 3C. The investment 34 is then allowed to set around the form 36 thereby creating a mold 38 which is the negative of form 36. For convenience of explanation, the cure of investment 34 is separated into a set period and a cure period.

Before the mold 38 is suitably prepared for subsequent use, the investment 34 must thoroughly hardened and cured. The process of hardening has two distinct phases. The first phase comprises that time during which the investment 34 is exothermically transformed from a liquid which has no shape, into a solid which maintains the shape imparted to it by device 10 This is called the setting process.

Figure 3D:
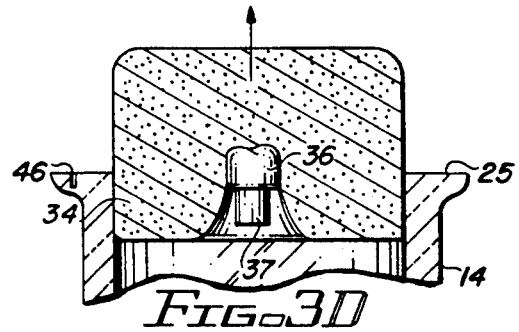
FIG. 3D is a cross-sectional view of a cured investment mold in the process of being withdrawn from the casting ring of FIG. 3C the casting ring has been detached from the sprue former.
Figure 3C:
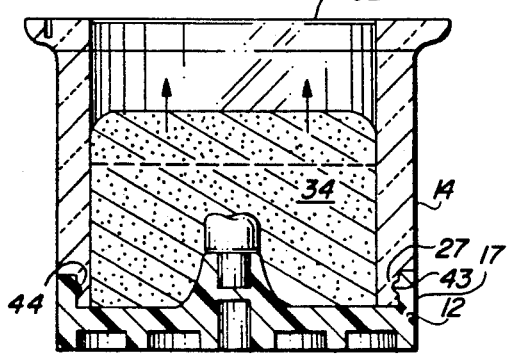
FIG. 3C is a cross-sectional view of the casting device of FIG. 3B showing a further fill of investment solution.
Figure 3E:
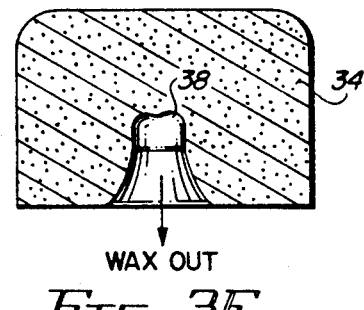
FIG. 3E is a cross-sectional view of the investment of FIG. 3D after the wax form has been removed therefrom.

After mold 38 is set, it is removed from assembly 10 as shown in FIG. 3D and allowed to cure for a suitable period which, for the investment solutions described above, is approximately 30-45 minutes. Cured mold 38 is then placed into an oven and heated to a temperature sufficient to liquefy the paraffin comprising form 36. When the liquefied paraffin has flowed out of mold 38 through the opening defined in the cured investment 34 corresponding to conical member 18, mold 38 becomes a true negative mold suitable for use in producing castings therefrom.

In one practice of the present invention, body portion 16 is preferably placed upon a flat stable surface. Base 12 is provided with a maximum of exposed surface area to facilitate heat transfer from the investment into the atmosphere. As shown in, FIGS. 2, 3A, 3B and 3C, the bottom surface 40 of body portion 16 is provided with a plurality of spaced concentric rings 41 to facilitate heat dissipation therefrom. The largest of the rings 41 is most easily congruent with the circumference of body portion 16. The spacing of rings 41 is ultimately dictated by the requirement of stability and heat transfer and may vary depending upon the diameter of the circle defined by body portion 16.

The upper surface 31 of body portion 16 is generally flat and featureless except for the placement of conical member 18 in the center thereof. Conical member 18 contains a cavity 22 which, as indicated, is dimensioned so that sprue or shank 37 of form 36 may be securely disposed therewithin.

The shape of casting ring 14 is also important to the successful practice of the invention, that is, the inside diameter of annular flange 25 is made slightly larger than the inside diameter of depending flange 27. The inward taper between flange 25 and flange 27, as defined by inside surface 33, will range from approximately 1 degree to approximately 10 degrees. This taper allows for the stress free expansion of investment 34 during the setting process, and for the easy removal of mold 38 from ring 14 after the investment is cured and the mold has set.

In certain larger molds, additional means of fixedly attaching two casting rings 14 together by mating annular flanges 25 may be necessary or desirable. For this eventuality, additional fastening means holes 46 are disposed in substantially equi-spaced relationship on the top surface of annular flange 25 to allow for the insertion of suitable auxiliary closing means such as pins (not shown) therebetween.

Several unobvious and unexpected advantages are gained by the use of a transparent elastic thermoplastic such as PVC in constructing base 12 and ring 14 to form assembly 10. First, by being transparent, form 36 may be more precisely placed within the assembly 10. Superior molds 38, and hence superior castings, result when positive form 36 is located where minimal thermal and investment expansion distortion occur during the exothermic curing process. In practice, this is accomplished by placing form 36 on conical member 18 which is disposed in the exact center of ring 14.

Second, transparency allows assembly 10 to be more accurately filled with investment 34. The use of either excess or insufficient amounts of investment solution 34 can have deleterious effects upon the dimensional accuracy of mold 38, and at a minimum involve extra cost and defective molds.

Third, the use of an elastic material, which is more deformable than the paraffin of form 36, minimizes the distortions created by the expansion of investment 34 during its exothermic setting. This dimensional accuracy is critical in the creation of dental castings and certain fine jewelry pieces. The stressed induced during setting are absorbed by the base 12 and ring 14 and not forced upon the softened paraffin of form 36. Finally, the thermoplastics used herewith are not attacked by the investment solution whereas the metal rings used heretofore are rapidly corroded and gain only a minimal shelf life.

From the foregoing, it is readily apparent that a useful embodiment of the present invention has been herein described and illustrated which fulfills all of the aforestated objectives a remarkably unexpected fashion. It is, of course, understood that such modifications, alterations and adaptations as may readily occur to the artisan confronted with this disclosure are intended within the spirit of this disclosure which is limited only by the scope of the claims appended hereto.

Accordingly, what is claimed is:

1. An assembly for producing high-precision molds for use in the preparation of lost wax castings, said assembly comprising: a casting ring; a preselected wax form, and a base member, said casting ring and said base member each being formed of a transparent resilient plastic material, said base member having form support means disposed therein for receiving and holding said preselected wax form thereupon, said casting ring having a body portion, a depending flange portion integrally formed with said body portion and inset therefrom to define a planar surface therebetween, and a peripheral groove defined in said flange portion in spaced generally parallel relationship to said planar surface, said body portion having an upper edge and an upper flange portion integrally formed with said upper edge and extending outwardly therefrom, said upper flange having a plurality of pin receiving means defined therein for securing another assembly thereto, said base member receiving and securing a portion of said casting ring therein in sealed engagement therewith to form a vessel therewith, said vessel being responsive to absorb the exothermic expansion of an investment solution disposed in said vessel while said investment solution is curing about said preselected form.

2. An assembly for producing high-precision molds for use in the preparation of lost wax castings, said assembly comprising: a casting ring; a preselected wax form; and a base member, said casting ring and said base member each being formed of a transparent resilient plastic material, said base member having form support means disposed therein for receiving and holding said preselected wax form thereupon and body portion having a perimeter and a flange member disposed on said perimeter and extending upwardly therefrom in circumscription about said form support means, said flange member having an upper edge, an inner surface and an outer surface, said inner surface having a head defined thereupon in spaced generally parallel relationship to said upper edge, said base member receiving and securing a portion of said casting ring therein in circumscribing sealed engagement to form a vessel therewith, said vessel being responsive to absorb the exothermic expansion of an investment solution disposed therein while said investment is curing about said preselected wax form to create a non-distorted pattern thereof.

3. An assembly according to claim 2 in which said casting ring comprises a body portion, a depending flange portion integrally formed with said body portion and inset from the outer surface thereof and defining a planar surface therebetween, a circumscribing groove defined in said flange portion in spaced generally parallel relationship to said planar surface.

4. An assembly according to claim 2 in which said body portion has an upper surface, a lower surface, and a plurality of concentric rings disposed upon said lower surface in generally normal relationship thereto.

5. An assembly according to claim 2 in which said form support means comprises a generally conical member having a base portion centrally disposed upon said body portion and extending upwardly therefrom, said conical member having a cavity therein for receiving and securing said preselected form.

6. An assembly according to claim 5 in which said body portion has an upper surface, a lower surface, and a plurality of concentric rings disposed upon said lower surface in generally normal relationship thereto.

7. An assembly according to claim 2 in which said casting ring comprises a body portion, a depending flange portion integrally formed with said body portion and inset therefrom to define a planar surface therebetween, and a peripheral groove defined in said flange portion in spaced generally parallel relationship to said planar surface.

8. An assembly according to claim 7 in which said depending flange portion is telescopically insertable within said base member for liquid tight sealing engagement therewith.

9. An assembly according to claim 7 in which said body portion comprises an upper edge and flange portion integrally formed with said upper edge and extending outwardly therefrom.

10. An assembly according to claim 9 in which said outwardly extending flange portion contains a plurality of pin receiving means for securing another assembly thereto.

* * * * *